(12) United States Patent
Abrams et al.

(10) Patent No.: US 6,238,927 B1
(45) Date of Patent: May 29, 2001

(54) REVERSE DISPLACEMENT ASSAY FOR DETECTION OF NUCLEIC ACID SEQUENCES

(75) Inventors: Ezra S. Abrams, W. Newtown; Philip W. Hammond, Ayer, both of MA (US)

(73) Assignee: Mosaic Technologies, Incorporated, Waltham, MA (US)

( * ) Notice: Subject to any disclaimer, the term of this patent is extended or adjusted under 35 U.S.C. 154(b) by 0 days.

(21) Appl. No.: 09/411,777

(22) Filed: Oct. 4, 1999

Related U.S. Application Data

(60) Provisional application No. 60/103,075, filed on Oct. 5, 1998.

(51) Int. Cl.[7] .............................. G01N 33/00; C12Q 1/68; C12P 19/34; C07H 21/04; B01D 57/02
(52) U.S. Cl. .............................. 436/94; 435/6; 435/91.1; 536/24.3; 204/456
(58) Field of Search .............................. 435/6, 91.1, 91.2, 435/183, 283.1, 975; 436/94, 501; 536/23.1, 24.3, 24.33, 25.3; 204/182.8

(56) References Cited

U.S. PATENT DOCUMENTS

| | | | |
|---|---|---|---|
| 4,725,536 | 2/1988 | Fritsch et al. | |
| 4,766,062 | * 8/1988 | Diamond et al. | 435/6 |
| 4,766,064 | 8/1988 | Williams et al. | 435/6 |

(List continued on next page.)

FOREIGN PATENT DOCUMENTS

| | | |
|---|---|---|
| 0 269 764 | 6/1988 | (EP) . |
| 0 330 185 | 8/1989 | (EP) . |
| 0 450 370 | 10/1991 | (EP) . |

(List continued on next page.)

OTHER PUBLICATIONS

Baba, Y. et al., "Base–sepcific separation of oligodeoxynucleotides by capillary affinity gel electrophoresis," *Electrophoresis* 19:433–436 (1998).

Biagioni, et al., "A New Method for the Preparation of DNA–Cellulose", *Analytical Biochemistry*, Academic Press, Inc. 89, 616–619 (1978).

Bille, V., et al., "Effect of the microenvironment on the kinetic properties of immobilized enzymes," *Eur. J. Biochem*, 180: 41–47 (1989).

Blajchman, M.A. and Ali, A.M., "Bacteria in the Blood Supply: An Overlooked Issue in Transfusion Medicine", *Blood Safety: Current Challenges*, pp. 213–227 (1992).

Bolton, E.T., and McCarthy, B.J., "A General Method For the Isolation of RNA Complementary to DNA," *Proc. Natl. Acad. Sci. USA*, 48: 1390–1397 (1962).

Brecher, M.E., et al., "Platelet Bacterial Contamination and the Use of a Chemiluminescence–Linked Universal Bacterial Ribosomal RNA Gene Probe," *Transfusion*, 34(9): 750–755 (1994).

(List continued on next page.)

*Primary Examiner*—W. Gary Jones
*Assistant Examiner*—Frank Lu
(74) *Attorney, Agent, or Firm*—Hamilton, Brook, Smith & Reynolds, P.C.

(57) ABSTRACT

The present invention pertains to a method and compositions for detecting the presence of a target nucleic acid in a test sample in which the sample to be tested for the presence of the target nucleic acid is introduced into a solution containing the probe-tether complex under conditions suitable for hybridization to occur between the first probe nucleic acid sequence and the target nucleic acid sequence so that the second tether nucleic acid sequence is displaced from the probe-tether complex, and a new complex is formed by the hybridization of the first probe nucleic acid sequence and the target nucleic acid sequence

38 Claims, 3 Drawing Sheets

U.S. PATENT DOCUMENTS

| | | | |
|---|---|---|---|
| 4,829,098 | 5/1989 | Hoffman et al. | 522/5 |
| 4,851,330 | 7/1989 | Kohne | 435/6 |
| 4,950,613 | 8/1990 | Arnold, Jr. et al. | 436/546 |
| 5,034,428 | 7/1991 | Hoffman et al. | 522/5 |
| 5,176,996 | 1/1993 | Hogan et al. | 435/6 |
| 5,215,882 | 6/1993 | Bahl et al. | 435/6 |
| 5,237,016 | 8/1993 | Ghosh et al. | 525/329.4 |
| 5,288,609 | 2/1994 | Engelhardt et al. | 435/6 |
| 5,288,611 | 2/1994 | Kohne | 435/6 |
| 5,310,650 | 5/1994 | McMahon et al. | 435/6 |
| 5,362,859 | 11/1994 | Zale | 530/413 |
| 5,478,893 | 12/1995 | Ghosh et al. | 525/329 |
| 5,482,836 | 1/1996 | Cantor et al. | 435/6 |
| 5,482,863 | 1/1996 | Knobel | 436/54 |
| 5,541,308 | 7/1996 | Hogan et al. | 536/23.1 |
| 5,605,662 | 2/1997 | Heller et al. | 422/68.1 |
| 5,610,287 | 3/1997 | Nikiforov et al. | 536/24.3 |
| 5,641,658 | 6/1997 | Adams et al. | 435/91.2 |
| 5,679,524 | 10/1997 | Nikiforov et al. | 435/6 |
| 5,679,773 | 10/1997 | Holmes | 530/334 |
| 5,741,639 | 4/1998 | Ensing et al. | 435/6 |
| 5,756,291 | 5/1998 | Griffin et al. | 435/6 |
| 5,932,711 * | 8/1988 | Boles et al. | 536/22.1 |

FOREIGN PATENT DOCUMENTS

| | | |
|---|---|---|
| 0 450 594 | 10/1991 | (EP). |
| 0 671 626 A1 | 9/1995 | (EP). |
| 0 703 296 A1 | 3/1996 | (EP). |
| H3 47097 | 2/1991 | (JP). |
| WO 87/03911 | 7/1987 | (WO). |
| WO 90/0758 | 7/1990 | (WO). |
| WO 91/08307 | 6/1991 | (WO). |
| WO 92/15712 | 9/1992 | (WO). |
| WO94/01446 | 1/1994 | (WO). |
| WO 94/06937 | 3/1994 | (WO). |
| WO 94/09156 | 4/1994 | (WO). |
| WO 94/16108 | 7/1994 | (WO). |
| WO 96/00795 | 1/1996 | (WO). |
| WO 97/27327 | 7/1997 | (WO). |
| WO 97/35033 | 9/1997 | (WO). |
| WO 97/41256 | 11/1997 | (WO). |
| WO 97/45554 | 12/1997 | (WO). |
| WO 97/45721 | 12/1997 | (WO). |
| WO 98/51823 | 11/1998 | (WO). |

OTHER PUBLICATIONS

Brecher, M.E., et al., "The Use of a Chemiluminescence–Linked Universal Bacterial Ribosomal RNA Gene Probe and Blood Gas Analysis for the Rapid Detection of Bacterial Contamination in White Cell–Reduced and Non-reduced Platelets," *Transfusion*, 33(6): 450–457 (1993).

Ellington, A.D., and Szostak, J.W., "In vitro selection of RNA molecules that bind specific ligands," *Nature*, 346 (6287): 818–822 (1990).

Forbes, B.A. and Granato, P.A., "Processing Specimens for Bacteria," *Bacteriology*, pp. 265–281.

Freier, S., et al., "The ups and downs of nucleic acid duplex stability: structure–stability studies on chemically–modified DNA:RNA duplexes," *Nucleic Acid Research* 25(22): 4429–4443 (1997).

Green, C., and Tibbetts, C., "Reaassociation rate limited displacement of DNA strands by branch migration," *Nucleic Acids Research*, 9(8): 1905–1918 (1981).

Hammond, P.W., et al., "Multiple Sequential Polynucleotide Displacement Reactions for Signal Amplification and Processing," U.S. Application Serial No., 09/188,086 filed Nov. 6, 1998.

Holtz, J.H., and Asher,S.A., "Polymerized colloidal crystal hydrogel films as intelligent chemical sensing materials," *Nature*, 389: 829–832 (1997).

Horejsi, V., and Kocourek, J., "Studies on Phytohemagglutinins XVIII. Affinity Electrophoresis of Phytohemagglutinins," *Biochimica et Biophysica Acta*, 336: 338–343 (1974).

Igloi, A., "Variability in the stability of DNA–peptide nucleic acid (PNA) single–base mismatched duplexes: Real– time hybridization during affinity electrophoresis in PNA– containing gels," *Proc. Natl. Acad. Sci. USA* 95:8562–8567 (Jul. 1998).

Iyer, M., et al., "Accelerated Hybridization of Oligonucleotides to Duplex DNA," *J. Biological Chemistry*, 270(24): 14712–14717 (1995).

Jarrett,H. W., "Affinity chromatography with nucleic acid polymers," *Journal of Chromatography*, 618, pp. 315–339, 1983. *Biomedical Applications*, Elsevier Science Publishers B.V. Amsterdam.

Joyce, G.F., "Amplification, mutation and selection of catalytic RNA," *Gene*, 82(1): 83–87 (1989).

Kenney, M., et al., Mutation Typing Using Electrophoresis and Gel–Immobilized Acrydite™ Probes, *BioTechniques*, 25: 516–521 (1998).

Klein, H.G., et al., "Current Status of Microbial Contamination of Blood Components: Summary of a Conference," *Transfusion*, 37: 95–101 (1997).

Klug, S.J., and Famulok, M., "All you wanted to know about SELEX," *Molecular Biology Reports* 20: 97–107 (1994).

Koroleva, O.N., et al., "The Construction of Mixed Polymers Consisting of DNA Fragments with Consensus Promoter Elements and Nonnucleotide Spacers," *Department of Chemistry and A.N. Belozersky Institute of Physico–Chemical Biology, M.V. Lomonosov Moscow State University, Moscow* 420–432 (1994).

Krishnan, L.A.G. and Brecher, M.E., "Transfusion–Transmitted Bacterial Infection," *Hematology/Oncology Clinics of North America*, 9(1): 167–185 (1995).

Maxwell, I.H., et al., "Assay of DNA–RNA hybrids by $S_1$ nuclease digestion and adsorption of DEAE–cellulose filters," *Nucleic Acids Research*, 5(6): 2033–2038 (1978).

Moody, H.M., et al., "Regiospecific inhibition of DNA duplication by antisense phosphate–methylated oligodeocynucleotides," *Nucleic Acids Research*, 17(12): 4769–4782 (1989).

Muscate, et al., "Capillary Affinity Gel Electrophoresis for Combined Size–and Sequence–Dependent Separation of Oligonucleotides," *Anal. Chem.* 70, pp. 1419–1424, 1998.

Nielsen, P.E., et al., "Sequence–Selective Recognition of DNA by Strand Displacement with a Thymine–Substituted Polyamide," *Science*, 254: 1497–1500 (1991).

Olenjnik, J., et al., "Photocleavable aminotag phorphoramidites for 5'–termini DNA/RNA labeling," *Nucleic Acids Research* 26(15): 3572–3576 (1998).

Ozaki, et al., "Affinity capillary electrophoresis using DNA conjugates," *Nucleic Acids Symposium Series*, Oxford University Press, No. 37, pp. 235–236, 1997.

Podzorski, R.P. and Persing, D.H., "Molecular Detection and Identification of Microorganisms," *Diagnostic Technologies in Clinical Microbiology*, pp. 130–157.

Quartin, R S. and Wetmur, J. G., "Effect of Ionic Strength on the Hybridization of Oligodeoxynucleotides with Reduced Charge Due to Methylphosphonate Linkages to Unmodified Oligodeoxynucleotides Containing the Complementary Sequence," *Biochemistry* 28, pp. 1040–1047, 1989 American Chemical Society.

Quesade, M.A., "Replaceable polymers in DNA sequencing by capillary electophoresis,"*Current Opinion in Biotechnology*, 8: 82–93 (1997).

Reinhartz, et al., "A novel rapid hybridization technique: paper chromatography hybridization assay (PACHA)," Elsevier Science Publishers B.V., pp. 221–226, 1993.

Rorer, Michelle L., "Battling Bacterial Contamination," *Advance/Laboratory*, 41–46 (1997).

Smithies, O., "An Improved Procedure for Starch–gel Electrophoresis: Further Variations in the Serum Proteins of Normal Individuals," *Biochem. J.*, 71(3): 585–587 (1959).

Timofeev, E.N., et al., "Regioselective immobilization of short oligonucleotides to acrylic copolymer gels," *Nucleic Acids Research*, 24(16): 3142–3148 (1996).

Tsurui, et al., "A rapid and efficient cloning method with a solid–phase DNA probe: application for cloning the 5'–Flanking region of the gene encoding human fibronectin," Elsevier Science Publishers B.F. (Biomedical Division), pp. 233–239 (1990).

Tuerk, C. and Gold, L., "Systematic Evolution of Ligands by Exponential Enrichment: RNA Ligands to Bacteriophage T4 DNA Polymerase," *Science*, 249: 505–510 (1990).

Tyagi, S., and Kramer, F.R., "Molecular Beacons: Probes that Fluoresce upon Hybridization," *Nature Biotechnology*, 14: 303–308 (1996).

Van Ness, J. et al., "A Versatile Solid Support System for Oligodeoxynucleotide Probe–Based Hybridization Assays," *Nucleic Acids Research*, 19(12): 3345–3350 (1991).

Vary, C.P.H., et al., "Nonisotopic Detection Methods for Strand Displacement Assays of Nucleic Acids," *Clinical Chemistry*, 32(9): 1696–1701 (1986).

Vary, C.P.H., "A homogeneous nucleic acid hybridization assay based on strand displacement," *Nucleic Acids Research*, 15(17): 6883–6897 (1987).

Wagner, S.J., et al., "Transfusion–Associated Bacterial Sepsis," *Clinical Microbiology Reviews*, 7(3): 290–302 (1994).

Wagner, R.W., "Gene inhibition using antisense oligodeoxynucleotides," *Nature*, 372: 333–335 (1994).

Wang, P., et al., "Biocatalytic plastics as active and stable materials for biotransformations," *Nature Biotechnology*, 15: 789–793 (1997).

Wetmur, James G., "Acceleration of DNA Renaturation Rates," Biopolymers, John Wiley and Sons, Inc., vol. 14., 2517–2524, 1975.

Wetmur, J., "DNA Probes: Applications of the Principles of Nucleic Acid Hybridization," *Critical Reviews in Biochemistry and Molecular Biology*, 26(3/4): 227–259 (1991).

Wieder, R., and Wetmur, J.G., "One Hundred–Fold Acceleration of DNA Renaturation Rates in Solution," Biopolymers, John Wiley and Sons, Inc., vol. 20, 1537–1547 (1981).

Yokota, H., and Oishi, M., "Differential cloning of genomic DNA: Cloning of DNA with an altered primary structure by in–gel competitive reassociation," *Proc. Natl. Acad. USA*, vol. 87, pp. 6398–6402 (1990). Biochemistry.

Yashima et al., Affinity gel electrophoresis of nucleic acids. Specific base– and shape–selective separation of DNA and RNA on polyacrylamide–nucleobase conjugated gel. J. Chromatograph A 654, 159–166, 1993.*

Vary. A homogeneous nucleic acid hybridization assay based on strand displacement. Nucleic Acids Res. 15, 6883–6897, 1987.*

Vary et al., Nonisotopic detection methods for strand displacement assays of nucleic acids. Clin. Chem. 32/9, 1696–1701, 1986.*

Green et al., Reassociation rate limited displacement of DNA strands by branch migration. Nucleic Acids Res. 24, 1905–1918, 1981.*

* cited by examiner

SEQUENCE LISTING

<160> NUMBER OF SEQ ID NOS: 3

<210> SEQ ID NO: 1
<211> LENGTH: 52
<212> TYPE: DNA
<213> ORGANISM: Artificial Sequence
<220> FEATURE:
<223> OTHER INFORMATION: target oligonucleotide

<400> SEQUENCE: 1
cacaagcggt ggagcatgtg gtttaattcg atgcaacgcg aagaaccta cc               52

<210> SEQ ID NO: 2
<211> LENGTH: 24
<212> TYPE: DNA
<213> ORGANISM: Artificial Sequence
<220> FEATURE:
<223> OTHER INFORMATION: oligonucleotide modified with 5' binding moiety

<400> SEQUENCE: 2
cacaagcggt ggagcatgtg gttt                                            24

<210> SEQ ID NO: 3
<211> LENGTH: 67
<212> TYPE: DNA
<213> ORGANISM: Artificial Sequence
<220> FEATURE:
<223> OTHER INFORMATION: fluorescently-labeled probe oligonucleotide

<400> SEQUENCE: 3
ggttcttcgc gttgcatcga attaaaccac atgctccacc gcttgtgcaa aaacgataaa     60
ccaacca                                                               67

REVERSE DISPLACEMENT ASSAY FOR DETECTION OF NUCLEIC ACID SEQUENCES

RELATED APPLICATIONS

This application claims the benefit of United States Provisional Application entitled "Reverse Displacement Assay for Nucleic Acid Targets", filed on Oct. 5, 1998 and assigned Ser. No. 60/103,075. The teachings contained within that application, including all text, figures and references cited therein, are hereby incorporated by reference in their entirety.

BACKGROUND OF THE INVENTION

The principle of hybridization is the property upon which most practical methods of detecting nucleic acid sequences are based. In general, methods for detecting the presence of particular target nucleic acid sequences involve employing a complementary sequence termed a probe, generally detectably labeled, and incubating this labeled probe sequence with the test sample thought to contain the target nucleic acid sequence. These complementary nucleic acid sequences hybridize to one another under suitable conditions to form probe-target hybridization complexes which can be identified through the presence of the detectable label. Various methods in which particular aspects of this basic process have been optimized for the purpose of addressing specific assay requirements have developed over time. (see Wetmur, 1991, *Critical Reviews in Biochemistry and Molecular Biology* 26, 227–259).

While some homogeneous phase hybridization assays permit detection of the hybridized probe-target complex without removal of excess unhybridized probe sequences present in the assay solution (see Tyagi and Kramer, 1996, *Nature Biotechnology* 14,303–308; Arnold, Waldrop, and Hanmmond, 1990, U.S. Pat. No. 4,950,613), very sensitive assays require separation of the hybridized complex from the unhybridized probe prior to the detection step. Many different methods have been employed to accomplish this separation, including several that rely on differences in physical characteristics between the two products. Other methods employ the use of a second nucleic acid sequence, described as a "capture" probe, for the purpose of separating the probe-target complex from the unhybridized probe. Capture probes are generally immobilized on a solid support and are selected to hybridize to a different portion of the target nucleic acid sequence than does the labeled probe. Thus, a tripartite capture probe-target-labeled probe complex forms which is bound to the solid support, while the unhybridized labeled probe remains unbound in solution, allowing the two products to be readily separated. Such assays are referred to as "sandwich" hybridizations (see, for example, Engelhardt and Rabbani, 1994, U.S. Pat. No. 5,288,609). Although widely used, these assays require a number of steps to perform and are quite time-consuming.

Alternative assay methods, termed displacement assays, were developed in an attempt to simplify the method of identifying nucleic acids. A schematic illustration of a standard displacement assay is depicted in FIG. 1 (see Diamond, S. E., et al., 1988, *U.S. Pat. No.* 4,766,062; Williams, J. I., et al. 1988, U.S. Pat. No. 4,766,064; Vary, 1987, *Nucleic Acids Res.* 15, 6883–6897; Vary et al., 1986, *Clinical Chemistry* 32, 1696–1701). In a standard displacement assay, a tether nucleic acid sequence, complementary to the target nucleic acid sequence, is hybridized to a shorter, detectably-labeled signal nucleic acid sequence, complementary to a specific subsequence of the tether sequence. The signal nucleic acid is fully base-paired with the tether nucleic acid in this signal-tether complex, but the longer tether nucleic acid retains a single-stranded region. Upon the introduction of a test sample containing the target nucleic acid, the target hybridizes to the single-stranded portion of the tether component. Since the target is homologous to the entire length of the tether, a homologous strand exchange reaction with the signal nucleic acid is initiated, and the target displaces the signal from the tether. This strand exchange reaction proceeds rapidly in the direction of signal nucleic acid displacement because the target is longer and forms a more stable duplex with the tether (see Green, C. and Tibbetts, C., 1981, *Nucleic Acids Res.* 9, 1905–1918). The amount of displaced labeled signal nucleic acid is measured to determine the amount of target nucleic acid in the sample. The tether component of the probe complex can also be linked to a solid support, so that separation of the solid and solution phases results in isolation of the signal nucleic acid.

Unfortunately, despite their advantages, standard displacement assays do have certain drawbacks. For example, when target nucleic acid hybridizes to a tether not hybridized to a signal nucleic acid, or when a displaced signal nucleic acid hybridizes to a tether nucleic acid which was not previously hybridized to a signal nucleic acid, a decrease in the detection signal produced per unit of target hybridized results. Moreover, if the hybridized complex is not stable, an undesirable background signal can be introduced, which complicates interpretation of the assay results and reduces the sensitivity of the assay.

SUMMARY OF THE INVENTION

The present invention is based, at least in part, on the discovery of a probe-tether complex useful in a novel reverse displacement assay. This assay eliminates many of the difficulties inherent in the standard displacement assay, while retaining the key advantages over other solution phase hybridization reactions. The probe-tether complex of the invention is formed by contacting a first probe nucleic acid sequence complementary to the target nucleic acid sequence with a second tether nucleic acid sequence complementary to at least one subsequence of the first nucleic acid sequence under conditions suitable for hybridization between the two sequences. The probe-tether complex of the invention contains at least one double stranded segment and at least one single stranded segment.

In one aspect, the present invention pertains to a method for detecting the presence of a target nucleic acid in a test sample in which the sample to be tested for the presence of the target nucleic acid is introduced into a solution containing the probe-tether complex, under conditions suitable for hybridization to occur between the first probe nucleic acid sequence and the target nucleic acid sequence, so that the second tether nucleic acid sequence is displaced from the probe-tether complex, and a second complex is formed by the hybridization of the first probe nucleic acid sequence and the target nucleic acid sequence. The presence of the target nucleic acid can then be detected in the test sample.

In a preferred embodiment, one of the nucleic acid sequences contains a detectable label. In a particularly preferred embodiment, the probe nucleic acid contains a detectable label.

In a preferred embodiment, one of the nucleic acids is immobilized on a solid support. In a particularly preferred embodiment, the tether nucleic acid sequence is immobilized on a solid support.

In a preferred embodiment, one of the nucleic acids is immobilized on an electrophoretic medium. In a particularly preferred embodiment, the tether nucleic acid sequence is immobilized on an electrophoretic medium.

In another aspect, the present invention pertains to a method of detecting a target nucleic acid sequence in a test sample in which the method utilizes multiple sequential nucleic acid displacement reactions. In this method, the sample to be tested for the presence of the target nucleic acid is introduced into a solution containing the probe-tether complex, under conditions suitable for hybridization to occur between the first probe nucleic acid sequence and the target nucleic acid sequence, so that the tether nucleic acid sequence is displaced from the probe-tether complex, and a second hybridization complex, termed a displacement complex, is formed by the hybridization of the probe nucleic acid sequence and the target nucleic acid sequence. The tether nucleic acid sequence displaced by the target nucleic acid sequence is then available to form a probe-tether complex and the remainder of the steps of the method can be repeated. The sequence of steps can be repeated as many times as desired. The presence of the target nucleic acid can then be detected in the test sample.

In a preferred embodiment, one of the nucleic acid sequences contains a detectable label. In a particularly preferred embodiment, the probe nucleic acid contains a detectable label.

In a preferred embodiment, one of the nucleic acids is immobilized on a solid support. In a particularly preferred embodiment, the tether nucleic acid sequence is immobilized on a solid support.

In a preferred embodiment, one of the nucleic acids is immobilized on an electrophoretic medium. In a particularly preferred embodiment, the tether nucleic acid sequence is immobilized on an electrophoretic medium.

In yet another aspect, the present invention pertains to a kit for detecting the presence of a target nucleic acid sequence in a test sample. The kit contains a first nucleic acid sequence component complementary to the target nucleic acid and a second nucleic acid sequence component complementary to at least one subsequence of the first probe nucleic acid component, selected such that when the components are combined under conditions suitable for hybridization, the first and second components form a probe-tether complex containing at least one double stranded segment and at least one single-stranded segment. In a preferred embodiment, one of the nucleic acids can be immobilized on a solid support.

DETAILED DESCRIPTION OF THE INVENTION

Figure 1:
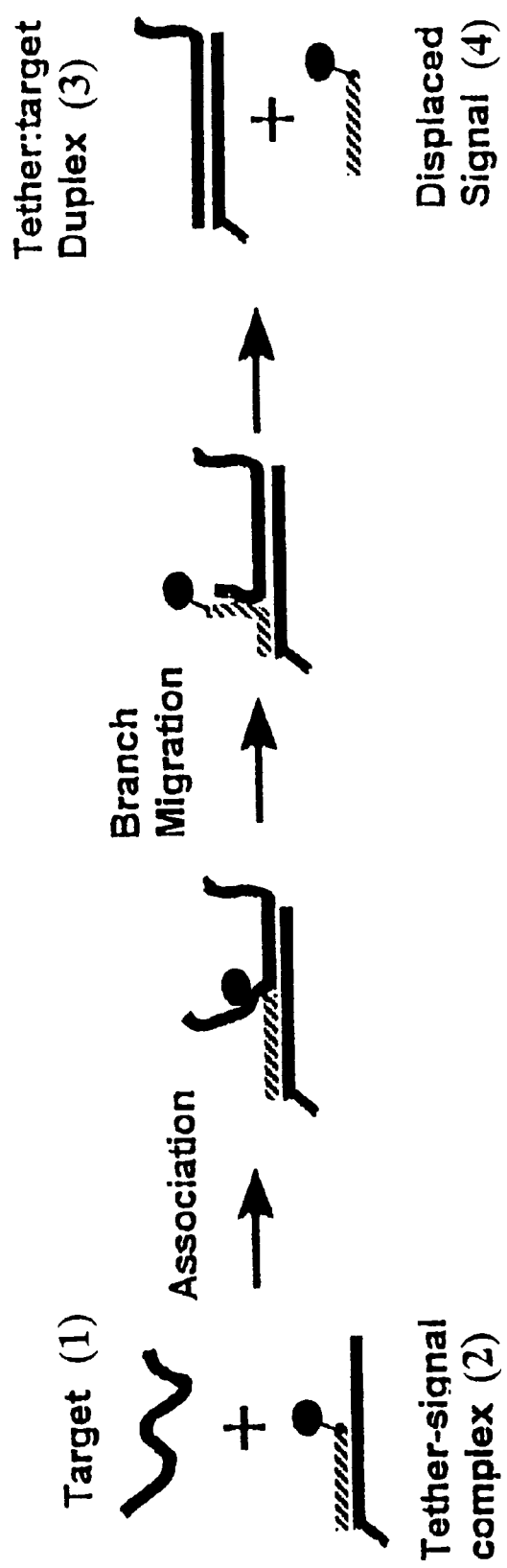
FIG. 1 is a schematic depiction of a standard displacement assay.

The invention described herein pertains to compositions and methods useful for analyzing nucleic acids in a variety of test samples. The methods of the invention described provide for a highly specific hybrization-based identification system for nucleic acids. The methods disclosed are based on the physical chemistry of hybridization between nucleic acids or polynucleotide sequence containing molecules. In particular, the methods utilize a reverse displacement type assay. The language "reverse displacement" is intended to include a reaction in which at least one product of the reaction is a complex formed by the hybridization of a probe nucleic acid and a target nucleic acid, and at least one product is formed by being displaced from a previous hybridization complex.

The language "test sample" is intended to include any sample that contains a protein, a nucleic acid or any charged species of molecule. For example, samples of biological origin such as blood, urine, other bodily fluids, cells (both plant and animal), cell extract, tissues and tissue extract are within the scope of the present invention. Samples from non-biological sources are also within the scope of the present invention.

The language "nucleic acid" or "polynucleotide sequence" and their respective plurals are used essentially interchangeably herein and are intended to include deoxyribonucleic acid (hereinafter "DNA") and ribonucleic acid (hereinafter "RNA"). Both single stranded and double stranded nucleic acids are embraced by this invention. Higher ordered structures of nucleic acids, for example, RNA that has folded upon its linear strand forming a secondary loop structure, are also within the scope of the present invention. Nucleic acid sequences encompassed by the present invention can be from about 3 to about 10,000 nucleotides in length. There is no absolute minimum or maximum length requirement for target nucleic acid sequences, however, a preferred range is from about 10 to about 2,000, preferably about 30 to about 1,000, most preferably about 30 to about 100. Preferably, the probe and tether nucleic acid sequences are from about 10 to about 2,000 nucleotides in length, and about 5 to about 2,000 nucleotides in length, respectively, most preferably about 20 to about 100 and 6 to about 100. It should also be understood that the nucleic acid sequences of the present invention may be embedded within longer strands of nucleic acids or associated with other molecules. The directionality of the nucleic acids of the current invention may be either 5' to 3' or the reverse, that is, 3' to 5'.

The language "base-pairing" is intended to include those reactions which occur in an antiparallel manner as well as those which occur in a parallel fashion. Base-pairing itself is understood to essentially follow a complementary pattern wherein a purine pairs with a pyrimidine via hydrogen bonds. More particularly, it is understood that complementary base-pairing of individual base pairs generally follows Chargaff's Rule wherein an adenine pairs with a thymine (or uracil) and guanine pairs with cytosine. However, there are modified bases which account for unconventional base-pairing and these are considered to be within the scope of the instant invention. The language "modified nucleic acid" is intended to include a DNA or RNA nucleic acid molecule that contains chemically modified nucleotides. The term "nucleic acid analogue" is intended to include non-nucleic acid molecules that can engage in base-pairing interactions with conventional nucleic acids. These modified bases and nucleic acid analogues are considered to be within the scope of the instant invention. For example, nucleotides containing deazaguaine and uracil bases can be used in place of guanine and thymine, respectively, to decrease the thermal stability of hybridized probes. Similarly, 5-methylcytosine can be substituted for cytosine in hybrids if increased thermal stability is desired. Modification to the sugar moiety can also occur and is embraced by the present invention. For example, modification to the ribose sugar moiety through the addition of 2'-O-methyl groups can be used to reduce the nuclease susceptibility of RNA molecules. Modifications occurring with different moieties of the nucleic acid backbone are also within the scope of this invention. For example, the use of methyl phosphate, methyl phosphonate or phosphorothioate linkages to remove negative charges from the phosphodiester backbone can be used.

The best known example of a nucleic acid analogue is peptide nucleic acid (PNA), in which standard DNA bases are attached to a modified peptide backbone comprised of repeating N-(2-aminoethyl)glycine units (Nielsen et al., *Science vol.* 254, pp. 1497–1500, 1991). The peptide backbone is capable of holding the bases at the proper distance to base pair with standard DNA and RNA single strands. PNA-DNA hybrid duplexes are much stronger than equivalent DNA-DNA duplexes, probably due to the fact that there are no negatively charged phosphodiester linkages in the PNA strand. In addition, because of their unusual structure PNAs are very resistant to nuclease degradation. The tight binding of PNA to natural nucleic acids suggests that it may be particularly useful in displacement assays. It will be apparent to those skilled in the art that similar design strategies can be used to construct other nucleic acid analogues that will have useful properties for displacement probe assays.

The language "hybridize" or "hybridization" is intended to include admixing of at least two nucleic acid sequences under conditions such that when at least two complementary nucleic acid sequences are present, they will form a double-stranded structure through base-pairing. The language "complement" or "complementary" is intended to describe nucleic acid sequences which can form a double-stranded structure through base-pairing. Mismatches are permitted in the instant invention. Nucleotide mismatch can affect the affinity between nucleic acid sequences. The greater the mismatch between nucleic acid sequences, generally the lower the affinity between them as compared to perfectly matched nucleic acid sequences. Generally, the greater the mismatch between nucleic acid sequences, the more readily hybridization that exists between them can be disrupted. When mismatches between base pairs are present, they generally account for no more than 5% of the region of base-pairing. Preferably, the degree of complementarity between hybridization partners is from about 100% to about 95%, most preferably about 100%.

Altering the temperature at which the hybridization reaction occurs is a common method for modulating hybridization complex binding affinity. For example, at temperatures above the melting temperature (Tm) of the hybridization complex, binding affinity will be low Similarly, at temperatures below the Tm, binding affinity will be substantially higher. Therefore, if the Tm of a hybridization complex containing mismatches is determined and compared with the Tms of complexes with shorter lengths of perfectly matched nucleotides, the effective pairing length of complexes with mismatches can be ascertained and applied to the present invention.

Figure 2:
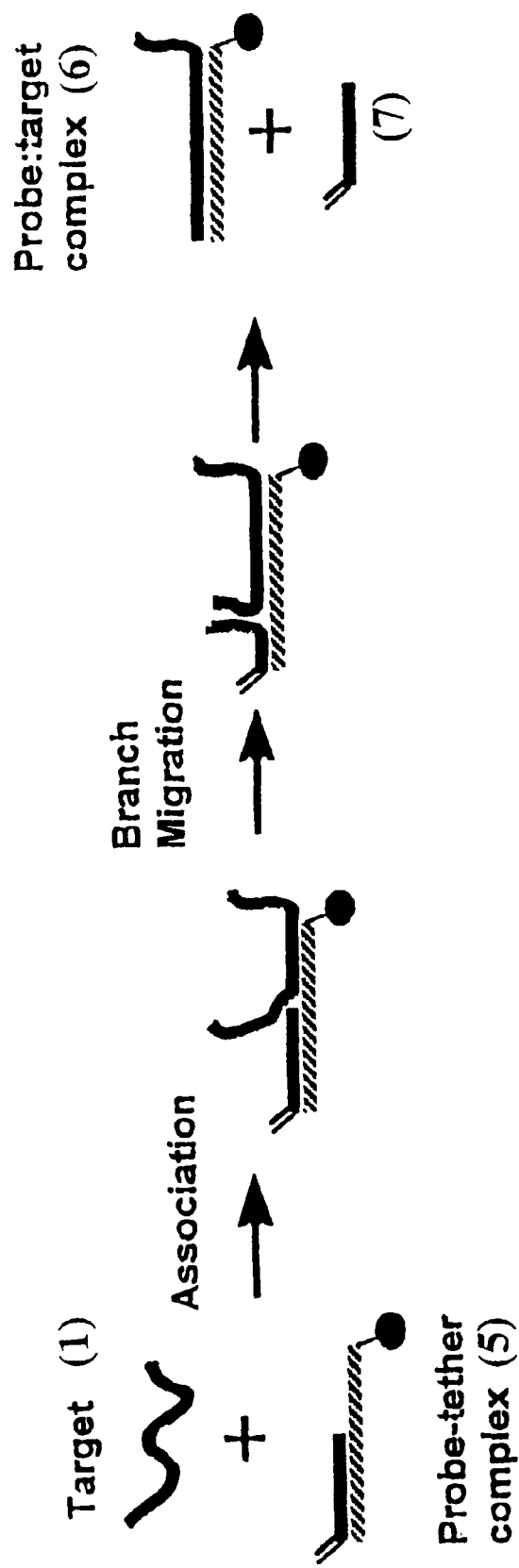
FIG. 2 is a schematic depiction of the reverse displacement assay of the present invention.
Figure 3:
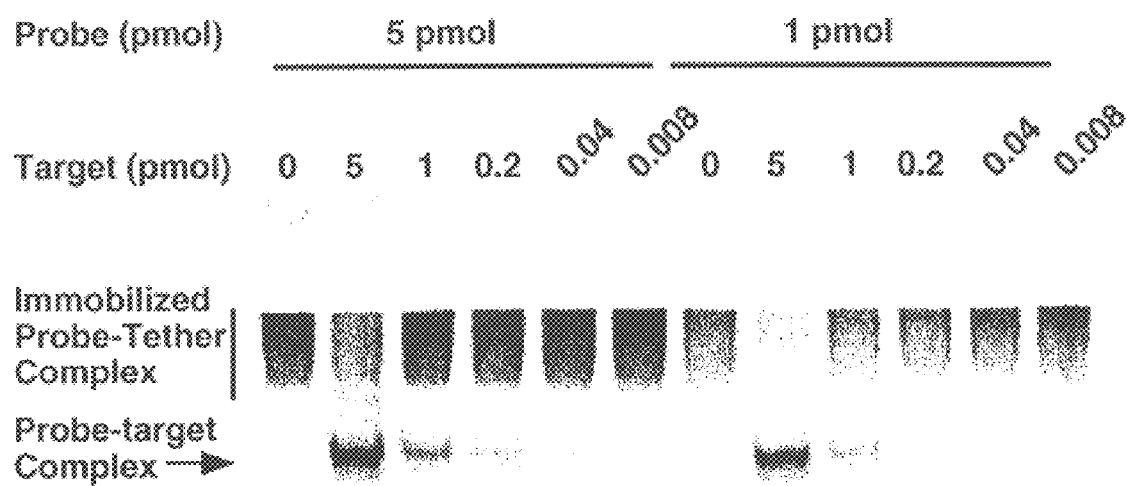
FIG. 3 is a depiction of a fluorimager scan of the results of the reverse displacement assay in a polyacrylamide gel as described in the Exemplification.

The methods described herein comprise sequential steps involving the formation of hybridization complexes and displacement of nucleic acid sequences. Reference is now made to the Figures. FIG. 1 depicts a standard displacement assay in which a target nucleic acid sequence (1) reacts with a tether-signal complex (2) to form a tether-target complex (3) product and a displaced signal (4) product. FIG. 2 depicts a reverse displacement assay of the invention in which a target nucleic acid sequence (1) reacts with a probe-tether complex (5) to form a probe-target complex (6) product and a displaced tether (7) product. FIG. 3 depicts a fluorimager scan of the results of the reverse displacement assay of the present invention in a polyacrylamide gel as described in the Exemplification. The probe nucleic acid sequence (8) is represented at the top of the figure with the target nucleic acid sequence (1) directly underneath. The probe-target complex (6) appears as a discrete band below the layer of immobilized probe-tether complex (5).

In the reverse displacement reaction of the invention, initially, a probe-tether nucleic acid complex is formed when a probe nucleic acid sequence and a tether nucleic acid sequence are combined, under conditions suitable for hybridization, such that the complex contains at least one double stranded segment and at least one single stranded segment. The first nucleic acid sequence is the probe nucleic acid sequence. The language "probe" is intended to include a nucleic acid sequence complementary to the target nucleic acid sequence. The second nucleic acid sequence is the tether nucleic acid sequence. The language "tether" is intended to include a nucleic acid sequence complementary to at least one subsequence of the probe nucleic acid. The language "subsequence" is intended to include any contiguous segment of a larger sequence. Thus, the tether nucleic acid is identical, or at least substantially similar in sequence, to a specific subsequence of the probe nucleic acid. The tether nucleic acid can contain more that one subsequence complementary to the probe nucleic acid. In addition, a complementary subsequence can be of any length. However, the entire length of the tether nucleic acid should not be complementary to the entire length of the probe nucleic acid.

When this probe-tether nucleic acid complex is combined in solution with the target nucleic acid under suitable conditions, the single stranded region of the probe-tether nucleic acid hybridizes with the target nucleic acid, and the probe nucleic acid is displaced from the tether nucleic acid by homologous strand exchange. One product of the reverse displacement reaction is a hybrid of the probe nucleic acid and the target nucleic acid. The language "probe-target complex" is intended to include the hybridized nucleic acid product of this reverse displacement reaction. A second product of the reverse displacement reaction is a displaced tether nucleic acid. A schematic illustration of a reverse displacement reaction of the invention is shown in FIG. 2.

As can be readily understood, two types of hybridization complexes are formed in the methods of the present invention. The first is a probe-tether hybridization complex and the second is a probe-target hybridization complex. The second complex can also be described as a displacement complex.

The probe-tether complex of the invention can be formed in an aqueous medium under conditions suitable for nucleic acid hybridization. Nucleic acid sequences are selected for this assay based upon their ability to hybridize to the other nucleic acid sequences utilized in the assay. The assay does not depend on a particular length requirement for any nucleic acid. Preferably, however, the binding region between the nucleic acid sequences undergoing hybridization to form a probe-tether complex is from about 5 to about 2,000 nucleotides in length, most preferably about 10 to 200 nucleotides in length. Additionally, for the probe-tether complex, the first probe nucleic acid sequence will have a degree of complementarity 95 to 100% with the target nucleic acid sequence, while the second tether nucleic acid sequence will have a degree of complementarity 95 to 100% to a subsequence of the first probe nucleic acid sequence, to the extent that such is required to facilitate the requisite chemical hybridization reaction.

A desirable temperature range during the formation of the probe-tether complex of the invention is from about 15° C. to about 90° C., depending upon the variables of other properties of the solution, such as ionic strength, pH, nucleic acid sequence concentration, degree of complementarity of the sequences, as well as other components of the aqueous medium that may affect melting temperatures. For a discussion and examples of suitable conditions see Wetmur, 1991, *Critical Reviews in Biochemistry and Molecular Biology*, 26:227–259.

The language "displacement complex", which is used interchangeably with the language "probe-target complex", is intended to include one product of a reaction event in which at least one nucleic acid sequence is displaced or removed from a hybridization complex. Such a complex is formed by the hybridization of two or more nucleic acid sequences. There is no particular length requirement for participating nucleic acid sequences; however, the length of the nucleic acid sequences do affect the stability of the hybridization complex. The size required to achieve a desired level of stability can be determined empirically. Preferably, the binding region between the nucleic acid sequences undergoing hybridization to form a displacement complex is from about 5 nucleotides to about 2,000 nucleotides in length, most preferably about 15 to 200. In the reverse displacement method of the present invention, the target nucleic acid sequence is one component of the displacement complex. The complex is formed as a result of the previous probe-tether complex coming into contact with the competing target nucleic acid sequence. Because the competing target nucleic acid sequence has a higher affinity for the probe nucleic acid sequence, the tether nucleic acid sequence is displaced from the complex. The product of this event is not only a new hybridization complex, but also, the displaced tether nucleic acid sequence.

The reaction events associated with a displacement complex can occur in an aqueous medium in which conditions are suitable for hybridization. The appropriate temperature to perform displacement reactions depends on the thermal stabilities of the hybrids present in the hybridization complex.

Either of the components of the probe-tether complex can be immobilized on a solid support through the use of a ligand. Preferably, the tether component is immobilized, since doing so maintains the advantages provided by the most efficient standard displacement assays. When the tether is immobilized, hybridization of the probe nucleic acid to the target nucleic acid will result in a release of the probe-target complex into solution. Thus, analysis of the isolated probe-target complex can be readily performed subsequent to separation of the solid and liquid phases. If the tether contains an affinity tag, separation of displaced probe from nondisplaced probe can be achieved following capture of the affinity tag on solid support material containing binding ligands specific for the tag.

The language "ligand" is intended to include any molecule that can form a specific binding complex with a target nucleic acid and that can be immobilized upon a suitable solid support.

One especially useful example of a ligand is a single stranded nucleic acid, which can bind, for example, to a complementary nucleic acid by hybridization. Single stranded nucleic acids can also be used for isolation of duplex nucleic acids by triplex formation (Hogan and Kessler, U.S. Pat. No. 5,176,966; Cantor, et al., U.S. Pat. No. 5,482,836). Double stranded nucleic acids can also serve as useful ligands for nucleic acid binding proteins, or for target nucleic acid sequences that bind to the ligand by triplex or tetraplex formation.

Nucleic acid aptamers (Tuerk and Gold, *Science* 1990 249, 5050–510,; Joyce, *Gene* 1989, 82, 83–87,; Ellington and Szostak, *Nature* 1990, 346, 818–822) can also be used as affinity ligands in the methods of the present invention. The language "aptamer" is intended to include a nucleic acid ligand that is selected for its ability to fit a target protein or other polymer. Aptamers can be selected against many kinds of targets, including proteins, small organic molecules, and carbohydrates (see Klug and Famulok, Molecular Biology Reports 1994, 20, 97–107). Thus, selection of aptamer ligands offers a simple and flexible mechanism for obtaining affinity ligands against virtually any target molecule.

Other useful ligands include proteins which can bind to specific targets. An especially useful class of protein ligands are antibody molecules, which can be elicited against a wide range of targets by immunization methods. Similarly, receptor proteins may be useful as ligands for purification and detection of targets that bind to or are bound by them.

Carbohydrates have been successfully used as affinity ligands for electrophoretic purification of lectins (Horejsi and Kocourek, *Biochim. Biophys. Acta* 1974, 336, 338–343), and may be useful for purification and detection of molecules that bind to specific carbohydrates or glycoproteins.

Many other types of immobilized ligands are possible including peptides, amino acids, nucleosides, nucleotides, small organic molecules, lipids, hormones, drugs, enzyme substrates, enzyme inhibitors, enzymes, coenzymes, inorganic molecules, chelating agents, macromolecular complexes, polysaccharides, monosaccharides, and others.

Immobilization of the nucleic acid can be accomplished by direct or indirect attachment to a solid support. The solid support can be a chromatographic support, a thin-layer plate or membrane, or electrophoretic polymeric media.

Any medium suitable for electrophoresis can be used in the methods of the present invention. In general, suitable media fall into two classes. The first includes media composed of gel-forming materials like crosslinked polyacrylamide and agarose. The second class includes media composed of solutions of linear noncrosslinked polymers such as polyacrylamide, poly(hydroxyethylcellulose), and poly (ethyleneoxide). The latter category is commonly used for capillary electrophoresis applications.

Direct attachment to the polymeric components of the medium can be accomplished by the formation of covalent bonds between the ligand and the polymer. Noncovalent binding between the ligand and polymer substituents can also be used. For instance, strong noncovalent binding provided by the widely-used biotinstreptavidin and digoxigenin-antidigoxigenin systems can be used to attach ligands to appropriately modified polymeric media. Covalent attachment is generally preferred.

Direct connection between the polymeric medium and the ligand are not strictly required. For instance, ligands can be attached to particulate supports, such as microspheres, and the particulate supports can be immobilized within the polymer medium by physical entrapment (Cantor, et al., U.S. Pat. No. 5,482,863). The particles may be macroscopic, microscopic, or colloidal in nature, (see Polysciences, Inc., 1995–1996 Particle Catalog, Warrington, Pa.).

In a similar manner, ligands can be attached to highly branched soluble polymers. Due to their branched shape, such ligand-polymer complexes display extremely large effective hydrodynamic radii and, therefore, will not migrate upon electrophoresis in many kinds of polymeric media of appropriately small pore size. Thus, they can be entrapped within the media in the same fashion as particulate supports.

Absolute immobilization of the ligand within the medium is not required for all embodiments of the invention. For many applications, it is sufficient that the mobility of the target is changed upon formation of a binding complex with the ligand. This condition can be satisfied by coupling the ligand to a medium component that has extremely low electrophoretic mobility. However, for efficient purification the change in mobility should be as large as possible. Therefore, media utilizing true immobilization of the ligand within the medium are generally preferred for use in this invention.

Commonly used gel media useful for the present invention include acrylamide and agarose gels. However, other materials may be used. Examples include modified acrylamides and acrylate esters (for examples see Polysciences, Inc., Polymer & Monomer catalog, 1996–1997, Warrington, Pa.), starch (Smithies, *Biochem. J.* 1959, 71, 585; product number S5651, Sigma Chemical Co., St. Louis, Miss.), dextrans (for examples see Polysciences, Inc., Polymer & Monomer Catalog, 1996–1997, Warrington, Pa.), and cellulose-based polymers (for examples see Quesada, *Current Opinions in Biotechnology* 1997, 8, 82–93). An acrylamide gel matrix such as Acrydite™ phosphoramidite media (Mosiac Technologies, Boston, Mass.) is a particularly preferred matrix. Any of these polymers can be chemically modified to allow specific attachment of ligands (including nucleic acids, proteins, peptides, organic small molecules, and others) for use in the present invention.

For some methods, it may be useful to use composite media, containing a mixture of two or more supporting materials. An example is the composite acrylamide-agarose gel. These gels typically contain from 2–5% acrylamide and 0.5%–1 % agarose. In these gels the acrylamide provides the chief sieving function, but without the agarose, such low concentration acrylamide gels lack mechanical strength for convenient handling. The agarose provides mechanical support without significantly altering the sieving properties of the acrylamide. In such cases, the nucleic acid can be attached to the component that confers the sieving function of the gel, since that component makes the most intimate contact with the solution phase target nucleic acid.

For capillary electrophoresis (CE) applications it is convenient to use media containing soluble polymers. Examples of soluble polymers that have proven to be useful for CE analyses are linear polymers of polyacrylamide, poly(N,N-dimethylacrylamide), poly(hydroxyethylcellulose), poly (ethyleneoxide) and poly(vinylalcohol) as described in Quesada, *Current Opinion in Biotechnology* 1997, 8, 82–93. Solutions of these polymers can also be used to practice the methods of the present invention.

Methods of coupling a variety of ligands to create affinity electrophoresis media are well known to those skilled in the art. Many ligands can be coupled to agarose, dextrans, cellulose, and starch polymers using cyanogen bromide or cyanuric chloride activation. Polymers containing carboxyl groups can be coupled to ligands that have primary amine groups using carbodiimide coupling. Polymers carrying primary amines can be coupled to amine containing ligands with glutaraldehyde or cyanuric chloride. Many polymers can be modified with thiol-reactive groups which can be coupled to thiol-containing ligands. Many other suitable methods are known in the literature. For examples, see Wong, "Chemistry of Protein Conjugation and Cross-linking", CRC Press, Boca Raton, Fla., 1993.

Methods for covalently attaching ligands by copolymerization with the polymeric material of the electrophoretic medium have also been developed. In this approach, ligands are chemically modified with a copolymerizable group. When such modified ligands are copolymerized with suitable mixtures of polymerizable monomers, polymeric media containing high concentrations of immobilized ligand can be produced. Examples of methods for covalently attaching nucleic acids to polymerizable chemical groups are found in U.S. patent application Ser. No. 08/812,105, filed Mar. 7, 1997, entitled "Nucleic Acid-Containing Polymerizable Complex," now U.S. Pat. No. 5,932,711 the teachings of which are expressly incorporated by reference herein, in their entirety. Similar methods have been used to immobilize proteins and small organic molecules within polymer layers and gels (Bille et al., *Eur. J. Biochem.* 1989, 180, 41–47; Wang et al., *Nature Biotechnology* 1997, 15, 789–793; Holtz and Asher, *Nature* 1997, 389, 829–832).

Other approaches for attaching nucleic acid probes to preformed polyacrylamide polymers, including gels or linear soluble polymers can be found in Timofeev et al., *Nucleic Acids Res.* 1996, 24, 3142–3148 and Ghosh and Fahy, U.S. Pat. No. 5,478,893.

One important advantage provided by the reverse displacement method of the present invention is that saturation of the tether nucleic acid with labeled probe nucleic acid is not required. Because the tether nucleic acid is not complementary to the target nucleic acid, uncomplexed tether nucleic acid will not hybridize with the target and, therefore, does not compete with target nucleic acid for hybridization with probe nucleic acids. In point of fact, since uncomplexed tether nucleic acids can hybridize to probe nucleic acids that have been released in a target-independent manner, it is likely that background noise is reduced in this assay. Furthermore, unhybridized tether nucleic acids cannot hybridize to probe-target hybrids, a significant difference from the corresponding situation in the standard displacement reaction.

In a preferred embodiment of the invention, the probe nucleic acid and/or the tether nucleic acid contains a detectable label. Most preferably, the probe nucleic acid contains a detectable label. The label can be bound ionically, covalently or in any other appropriate manner known in the art. The label is preferably bound to any region of the nucleic acid comprising the probe or tether nucleic acid sequences. The language "label" is intended to include those which directly utilize radioactive isotopes, fluorescent moieties, chemiluminescent moieties, and direct enzyme conjugates, as well as indirect labels, such as affinity labels for use with secondary or tertiary labeled molecules. Because the reverse displacement assay is not label-specific, any practicable label known to those of skill in the art is suitable for use with the assay.

Detection of the target nucleic acid may be accomplished in a variety of ways, but generally through detecting and/or measuring the value or change in value of any chemical or physical property of the product of the reverse displacement assay. Examples of physical properties suitable for use in detection and/or measurement include mass or density properties as determined by mass spectrometry or plasmon resonance, optical properties as determined by methods detecting emission, absorption, fluorescence, phosphorescence, luminescence, chemiluminescence, polarization, and refractive index changes, or other known techniques, electrical properties as determined by methods detecting conductivity, absorption or emission of other electromagnetic energy, radioactive properties, as well as induced changes in solution properties such as viscosity, turbidity, and optical rotation.

The reverse displacement assay as described above and illustrated in FIG. 2 includes a single displacement reaction. However, multiple sequential reactions are also within the scope of the present invention. In a reaction of this type, for example, a probe nucleic acid may be affinity labeled with a single-stranded nucleic acid tail. The probe-target complex may then be transferred to a secondary reaction area where this tail serves as the target for a second reverse displacement reaction.

Moreover, several cycles of probe and displacement complex formation, generating multiple displacement nucleic acid sequences in which one of the displaced nucleic acid sequences is identical to an original nucleic acid sequence, thereby facilitating cycling back to the first displacement complex and proceeding through the sequential hybridization and displacement cycles again can be performed. This process of recycling through probe and displacement complex formation provides for the amplification of assay signal prior to detection. The use of such multiple sequential displacement reactions has been previously described in co-pending U.S. patent application with Ser. No. 09/188,086 entitled "Multiple Sequential Polynucleotide Displacement Reactions for Signal Amplification and Processing," filed on Nov. 6, 1998, the teachings of which are expressly incorporated by reference herein in their entirety.

The present invention further pertains to a kit used for determining the presence of a target nucleic acid sequence within a test sample. The kit contains a first probe nucleic acid sequence component complementary to the target molecule and a second tether nucleic acid sequence component complementary to at least one subsequence of the probe component. The first and second components are selected such that when admixed, under conditions suitable for hybridization, the first and second components form a probe-tether complex containing at least one double stranded segment and at least one single stranded segment. The components may be provided singly or in combination. The kit may also include additional components. In a preferred embodiment, the probe and/or the tether component are detectably labeled. In a most preferred embodiment, the probe component is detectably labeled.

The invention is further illustrated by the following non-limiting example. The contents of all the patents, patent applications and other references cited herein are expressly incorporated by reference in their entireties.

EXEMPLIFICATION

The reverse displacement assay of the invention was demonstrated as follows. A naturally occurring sequence from the 16S rRNA subunit of *E. Coli* was selected as the target nucleic acid. A synthetic DNA oligonucleotide was used as a model target, 5'-CACAAGCGGTGG-AGCATGTGGTTTAATTCGATGCAACGC-GAAGAACCTTACC (SEQ ID NO:1). The unlabeled oligonucleotide tether 5'-Ac-CACAAGCGGTGG AGCATGTGGTTT (SEQ ID NO:2) was synthesized, where Ac represents an Aciydite™ phosphoramidite. The Acrydite™ group allows immobilization in an acrylamide gel matrix by co-polymerization. A fluorescently labeled probe oligonucleotide was synthesized with the sequence 5'-cy3-GGTTCTTCGCGTTGCATCGAATTAAACCACATGCTC CACCGCTTGTGCAAAAACGATAAACCAACCA (SEQ ID NO:3), of which the first forty-seven (47) nucleotides are complementary to the target. The last twenty (20) nucleotides were added as an affinity tag to allow the probe-target complex to be captured after the displacement reaction, although the tag was not utilized in this experiment.

The unlabeled tether oligonucleotide was copolymerized at a concentration of 10.0 μM in a polyacrylamide slab gel (10.0 cm×10.0 cm×0.8 mm) as a band approximately 1.0 cm wide extending across the width of the gel. The labeled oligonucleotide probe was then bound to this immobilized tether by electrophoresing either 1.0 pmol or 5.0 pmol through the gel at 50 V for 30 minutes. Unbound probe oligonucleotide and non-immobilized tether were removed from the gel by electrophoresing in the reverse direction at 200 V for 1 hour. Samples were then prepared that contained 0.0, 5.0, 1.0, 0.2, 0.04 or 0.008 pmol of the synthetic target. These samples were loaded on the gel and electrophoresed in the forward direction at 50 V for 1 hour. The gel was subsequently scanned using a Molecular Dynamics Fluorimager and the results are shown in FIG. 3. The complex of target with labeled probe appears as a discrete band below the layer of immobilized tether oligonucleotide with bound labeled probe The amount of probe-target complex was found to be linearly dependent on the amount of target loaded in each lane of the gel.

This experiment clearly demonstrates that a saturated layer is not needed for this new assay method. In addition, labeled oligonucleotide that dissociates from the immobilized oligonucleotide in a non-target dependent manner was rebound at a new site lower in the immobilized oligonucleotide layer. This decreases the background in the assay.

EQUIVALENTS

While this invention has been particularly shown and described with reference to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivlents are intended to be encompassd by the scope of the claims.

What is claimed is:

1. A method of detecting the presence or absence of a target nucleic acid in a test sample comprising the following steps:

forming a probe-tether complex by contacting a probe nucleic acid comprising a nucleotide sequence complementary to at least one subsequence of the nucleotide sequence of the target nucleic acid with a tether nucleic acid comprising a nucleotide sequence complementary to at least one subsequence of the nucleotide sequence of the probe nucleic acid, wherein a portion of the probe sequence complementary to the target sequence is also a portion of the probe sequence complementary to the tether sequence and, wherein the tether nucleic acid is immobilized on an electrophoretic polymeric medium, under conditions suitable for hybridization between the probe and tether nucleic acids, thereby forming a probe-tether complex in which the probe forms at least one double stranded nucleic acid segment hybridized to the tether and at least one single stranded nucleic acid segment not hybridized to the tether, wherein both probe segments are complementary to the target sequence;

introducing the test sample into the electrophoretic medium containing the probe-tether complex, under conditions suitable for migration of the target nucleic acid through the electrophoretic medium and hybridization between the probe nucleic acid and the target nucleic acid, thereby displacing the tether nucleic acid from the probe-tether complex;

forming a probe-target complex by contacting the probe-tether complex with the target nucleic acid, under conditions suitable for selective hybridization between the probe nucleic acid and the target nucleic acid, thereby forming a probe-target complex; and detecting the presence of the probe-target complex, wherein the presence of the probe-target complex is indicative of the presence of the target nucleic acid in the test sample.

2. The method of claim 1, wherein one of the nucleic acids contains a detectable label.

3. The method of claim 2, wherein the probe nucleic acid contains a detectable label.

4. The method of claim 3, wherein the mode of detecting the signal is selected from the group consisting of mass spectrometry, plasmon resonance, optical emission, absorption, fluorescence, phosphorescence, luminescence, chemiluminescence, polarization, refractive index changes, electrical conductivity, radioactivity, turbidity and optical rotation.

5. The method of claim 1, wherein the nucleic acids forming the probe-tether complex are selected from the group consisting of nucleic acids, modified nucleic acids and nucleic acid analogs.

6. The method of claim 1, wherein the electrophoretic medium is selected from the group consisting of polyacrylamide gel, starch gel and agarose gel.

7. The method of claim 1, wherein the probe subsequence complementary to the tether sequence is contained within the probe sequence complementary to the target sequence.

8. The method of claim 1, wherein the amount of target present in the test sample is measured.

9. The method of claim 1, wherein the displacement of the tether nucleic acid and the formation of the probe-target complex occur essentially simultaneously.

10. The method of claim 1, wherein the tether nucleic acid is immobilized to the polymeric medium with a thiol or a disulfide bond.

11. The method of claim 1, wherein the tether nucleic acid is immobilized to the polymeric medium with an amide bond.

12. The method of claim 1, wherein the tether nucleic acid is immobilized by copolymerization with the polymeric medium.

13. The method of claim 1, wherein the polymeric medium comprises acrylamide.

14. The method of claim 1 further comprising a step of electrophoretically separating a displaced probe-target complex from the immobilized probe-tether complex.

15. The method of claim 1 further comprising a step of eluting the target-probe complex from the electrophoretic medium.

16. The method of claim 15, wherein the mode of detecting the signal is selected from the group consisting of mass spectrometry, plasmon resonance, optical emission, absorption, fluorescence, phosphorescence, luminescence, chemiluminescence, polarization, refractive index changes, electrical conductivity, radioactivity, viscosity, turbidity and optical rotation.

17. A method of detecting the presence or absence of a target nucleic acid in a test sample comprising the following steps:

immobilizing a tether nucleic acid comprising a nucleotide sequence complementary to at least one subsequence of the nucleotide sequence of a probe nucleic acid comprising a nucleotide sequence complementary to at least one subsequence of the nucleotide sequence of the target nucleic acid on an electrophoretic polymeric medium, wherein a portion of the probe sequence complementary to the target sequence is also a portion of the probe sequence complementary to the tether sequence and;

forming a probe-tether complex by contacting the probe nucleic acid with the tether nucleic acid, under conditions suitable for hybridization between the probe and tether nucleic acids, thereby forming a probe-tether complex in which the probe forms at least one double stranded nucleic acid segment hybridized to the tether and at least one double stranded nucleic acid segment not hybridized to the tether, wherein both probe segments are complementary to the target sequence;

introducing the test sample into the electrophoretic medium containing the probe-tether complex, under conditions suitable for migration of the target nucleic acid through the electrophoretic medium and hybridization between the probe nucleic acid and the target nucleic acid, thereby displacing the tether nucleic acid from the probe-tether complex;

forming a probe-target complex by contacting the probe-tether complex with the target nucleic acid, under conditions suitable for selective hybridization between the probe nucleic acid and the target nucleic acid, thereby forming a probe-target complex; and detecting the presence or absence of the probe-target complex, wherein the presence of the probe-target complex is indicative of the presence of the target nucleic acid in the test sample.

18. The method of claim 17, wherein the displacement of the tether nucleic acid and the formation of the probe-target complex occur essentially simultaneously.

19. The method of claim 17, wherein one of the nucleic acids contains a detectable label.

20. The method of claim 17, wherein the probe nucleic acid contains a detectable label.

21. The method of claim 17, wherein the nucleic acids forming the probe-tether complex are selected from the group consisting of nucleic acids, modified nucleic acids and nucleic acid analogs.

22. The method of claim 21, wherein the probe subsequence complementary to the tether sequence is contained within the probe sequence complementary to the target sequence.

23. The method of claim 17, wherein the amount of target present in the test sample is measured.

24. The method of claim 17, wherein the tether nucleic acid is immobilized to the polymeric medium with a thiol or disulfide bond.

25. The method of claim 17, wherein the tether nucleic acid is immobilized to the polymeric medium with an amide bond.

26. The method of claim 17, wherein the tether nucleic acid is immobilized by copolymerization with the polymeric medium.

27. The method of claim 17, wherein the polymeric medium comprises an acrylamide.

28. The method of claim 17 further comprising a step of electrophoretically separating a displaced probe-target complex from the immobilized probe-tether complex..

29. The method of claim 17 further comprising a step of eluting the target-probe complex from the electrophoretic medium.

30. The method of claim 29, wherein the mode of detecting the signal is selected from the group consisting of mass spectrometry, plasmon resonance, optical emission, absorption, fluorescence, phosphorescence, luminescence, chemiluminescence, polarization, refractive index changes, electrical conductivity, radioactivity, viscosity, turbidity and optical rotation.

31. A method of detecting the presence or absence of a target nucleic acid in a test sample comprising the following steps:

forming a probe-tether complex by contacting a probe nucleic acid comprising a nucleotide sequence complementary to at least one subsequence of the nucleotide sequence of the target nucleic acid with a tether nucleic acid comprising a nucleotide sequence complementary to at least one subsequence of the nucleotide sequence of the probe nucleic acid, wherein a portion of the probe sequence complementary to the target sequence is also a portion of the probe sequence complementary to the tether sequence and, wherein the tether nucleic acid is immobilized on an electrophoretic polymeric medium, under conditions suitable for hybridization between the probe and tether nucleic acids, thereby forming a probe-tether complex in which the probe forms at least one double stranded nucleic acid segment hybridized to the tether and at least one single stranded nucleic acid segment not hybridized to the tether, wherein both probe segments are complementary to the target sequence;

introducing the test sample into the electrophoretic medium containing the probe-tether complex, under conditions suitable for migration of the target nucleic acid through the electrophoretic medium and selective hybridization between the probe nucleic acid and the target nucleic acid, thereby displacing the tether nucleic acid from the probe-tether complex; and detecting the presence of the probe-target complex, wherein the presence of the probe-target complex is indicative of the presence of the target nucleic acid in the test sample.

32. A kit for detecting the presence of a target nucleic acid in a test sample comprising:

a probe nucleic acid component comprising a nucleotide sequence complementary to at least one subsequence of the nucleotide sequence of the target molecule wherein a portion of the probe sequence complementary to the target sequence is also a portion of the probe sequence complementary to a tether sequence; and a tether nucleic acid component comprising a nucleotide sequence complementary to at least one subsequence of the nucleotide sequence of he probe component, wherein said tether nucleic acid is immobilized to an electrophoretic medium, wherein the medium is a formed gel or a polymer solution; and wherein, when combined under conditions suitable for hybridization, the probe and tether components form a probe-tether complex in which the probe forms at least one double stranded segment with the tether component and retains at least one single-stranded segment, wherein both segments of the probe are complementary to the target molecule.

33. The kit of claim 32 further comprising a component with a detectable label.

34. 19. The kit of claim 32, wherein the components of the probe-tether complex are selected from the group consisting of nucleic acids, modified nucleic acids and nucleic acid analogs.

35. The kit of claim 32, wherein the moiety forms a thiol or disulfide bond with the polymeric medium.

36. The kit of claim 32, wherein the moiety forms an amide bond with the polymeric medium.

37. The kit of claim 32, wherein the moiety copolymerizes with the polymeric medium.

38. The kit of claim 32, wherein the polymeric medium comprises acrylamide.

* * * * *